US006248794B1

United States Patent
Gieskes (10) Patent No.: US 6,248,794 B1
(45) Date of Patent: Jun. 19, 2001

(54) INTEGRATED PROCESS FOR CONVERTING HYDROCARBON GAS TO LIQUIDS

(75) Inventor: Thomas Gieskes, La Habra Heights, CA (US)

(73) Assignee: Atlantic Richfield Company, Chicago, IL (US)

( * ) Notice: Subject to any disclaimer, the term of this patent is extended or adjusted under 35 U.S.C. 154(b) by 0 days.

(21) Appl. No.: 09/369,045

(22) Filed: Aug. 5, 1999

(51) Int. Cl.[7] .................. C07C 27/00; C07C 273/00; C01C 1/04
(52) U.S. Cl. .................. 518/700; 518/702; 518/703; 518/704; 564/65; 423/359
(58) Field of Search .................. 518/700, 702, 518/703, 704; 564/65; 423/359

(56) References Cited

U.S. PATENT DOCUMENTS

| 5,733,941 | 3/1998 | Waycuilis . |
| 6,011,073 | 4/2000 | Agee et al. . |

*Primary Examiner*—Samuel Barts
*Assistant Examiner*—J. Parsa
(74) *Attorney, Agent, or Firm*—F. Lindsey Scott; Thomas A. Yassen (57) ABSTRACT

The present invention is an integrated process for converting light hydrocarbon gas to heavier hydrocarbon liquids. In each embodiment, a Fischer-Tropsch (FT) process comprising a thermal reformer and a reactor containing an FT catalyst is combined with one or more additional processes to achieve operational synergies. In a first embodiment, an FT process is integrated with a cryogenic liquefied natural gas (LNG) process wherein tail gas from the FT reaction is used to drive a refrigeration compressor in the LNG process. The tail gas, optionally supplemented with natural gas, may be fed directly to a gas turbine or may be combusted in steam boiler, which in turn provides steam to a steam turbine. The natural gas may be processed prior to its being fed to the LNG process and the FT process in order to remove any impurities and/or condensate. The process may be further integrated with a fertilizer production process comprising an ammonia synthesis process and a urea synthesis process. To produce ammonia, hydrogen separated from synthesis gas produced in a primary and/or secondary reformer in the FT process is combined with nitrogen produced in the LNG process. Nitrogen may also be supplied to the ammonia synthesis process from an optional air separation process, which also provides oxygen enrichment to the thermal reformer in the FT process. To produce urea, the ammonia is subsequently reacted with carbon dioxide removed during processing of the gas prior to its liquefaction. The integrated FT/LNG/Fertilizer process may be further integrated with a carbon dioxide removal process which separates flue gas from a gas turbine or steam generator driving the refrigeration compressor in the LNG process into nitrogen which is used in the ammonia synthesis process and carbon dioxide which is used in the urea synthesis unit. Alternatively, the FT process may be integrated directly with the fertilizer production process, in the absence of an LNG process. In an alternative embodiment, an FT process is integrated with a methanol synthesis process wherein tail gas from the FT reaction is used to fuel burners in a secondary thermal reformer.

48 Claims, 7 Drawing Sheets

INTEGRATED PROCESS FOR CONVERTING HYDROCARBON GAS TO LIQUIDS

BACKGROUND OF THE INVENTION

The present invention relates to a process for converting light hydrocarbon gas to a heavier hydrocarbon liquid, and, more particularly, to a gas conversion process employing a thermal reformer and a Fischer-Tropsch reactor.

Natural gas is often plentiful in regions where it is uneconomical to develop the reserves due to the lack of local markets for the gas or the high cost of transporting the gas to distant markets. An alternative is to produce the natural gas and convert it locally to a liquid hydrocarbon product for more cost-effective transportation. Processes for converting light hydrocarbon gases, such as natural gas, to heavier hydrocarbon liquids are generally known in the prior art. Such processes typically involve the indirect conversion of methane to synthetic paraffinic hydrocarbon compounds, wherein methane is first converted to a synthesis gas, commonly referred to as syngas and comprising hydrogen and carbon monoxide, followed by conversion of the synthesis gas to synthetic paraffinic hydrocarbon compounds via a Fischer-Tropsch catalyzed reaction. Inefficiency of the Fischer-Tropsch process is a drawback in that the value of the conversion products may not justify the cost associated with building and operating the conversion process. Therefore, a need exists for a more efficient process for the conversion of gas to liquid hydrocarbons. Integration of a Fischer-Tropsch process with other process units in accordance with this invention greatly improves the overall economics of converting gas to liquid hydrocarbons by reducing capital and operating expenses.

SUMMARY OF THE INVENTION

The present invention is an integrated process for converting light hydrocarbon gas to heavier hydrocarbon liquids. In each embodiment, a Fischer-Tropsch (FT) process comprising a thermal reformer and a reactor containing an FT catalyst is combined with one or more additional processes to achieve operational synergies.

In a first embodiment, an FT process is integrated with a cryogenic liquefied natural gas (LNG) process wherein tail gas from the FT reaction is used to drive a refrigeration compressor in the LNG process. The tail gas, optionally supplemented with natural gas, may be fed directly to a gas turbine or may be combusted in steam boiler, which in turn provides steam to a steam turbine. The natural gas may be processed prior to its being fed to the LNG process and the FT process in order to remove any impurities and/or condensate. The process may be further integrated with a fertilizer production process comprising an ammonia synthesis process and a urea synthesis process. To produce ammonia, hydrogen separated from synthesis gas produced in a primary and/or secondary reformer in the FT process is combined with nitrogen produced in the LNG process. Nitrogen may also be supplied to the ammonia synthesis process from an optional air separation process, which also provides oxygen enrichment to the thermal reformer in the FT process. To produce urea, the ammonia is subsequently reacted with carbon dioxide removed during processing of the gas prior to its liquefaction. The integrated FT/LNG/Fertilizer process may be further integrated with a carbon dioxide removal process which separates flue gas from a gas turbine or steam boiler driving the refrigeration compressor in the LNG process into nitrogen which is used in the ammonia synthesis process and carbon dioxide which is used in the urea synthesis unit. Alternatively, the FT process may be integrated directly with the fertilizer production process, in the absence of an LNG process.

In an alternative embodiment, an FT process is integrated with a methanol synthesis process wherein tail gas from the FT reaction is used to fuel burners in a secondary thermal reformer.

DESCRIPTION OF THE DRAWINGS

The actual construction, operation, and apparent advantages of the present invention will be better understood by referring to the drawings which are not necessarily to scale and in which like numerals refer to like parts.

DETAILED DESCRIPTION OF THE INVENTION

Figure 1A:
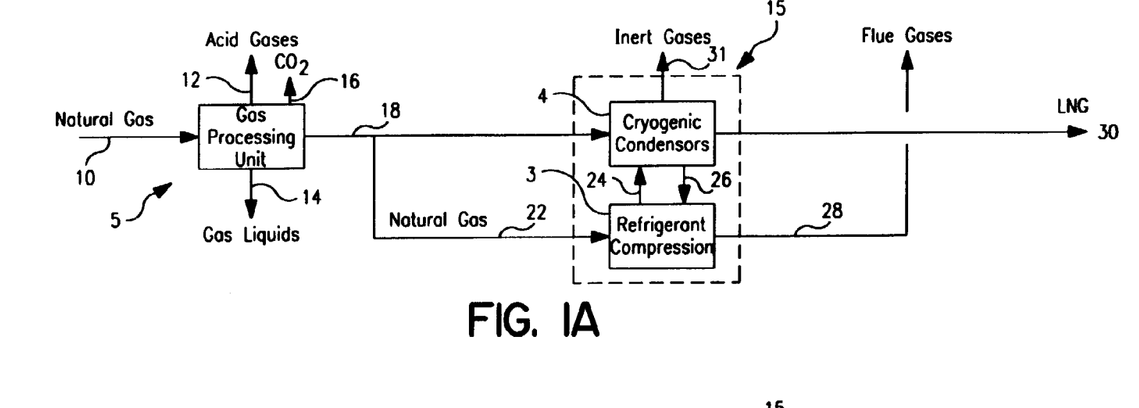
FIG. 1A is a process flow diagram of a non-integrated process for liquefying natural gas.

FIG. 1A shows a non-integrated LNG process of the type well known in the art comprising a gas processing unit 5 and a cryogenic liquefaction unit 15. Untreated (i.e., raw) natural gas is fed via stream 10 to gas processing unit 5, wherein carbon dioxide is removed via stream 16, acid gases such as hydrogen sulfide are removed via stream 12, and entrained liquids such as water and condensed hydrocarbons are separated and recovered via stream 14. The need for and scope of gas processing varies depending upon the characteristics of the raw gas being recovered, and will be readily apparent to one skilled in the art throughout the various embodiments disclosed herein. Likewise, the use of either raw natural gas, treated natural gas, or a combination thereof as feed to the various process units disclosed herein will be readily apparent, and alternative embodiments are shown in the various Figures.

After processing, natural gas stream 18 is fed to a cryogenic liquefaction unit wherein the natural gas is subjected to refrigeration and is liquefied. Refrigerant, typically a mixture of propane with other known mixed refrigerants (MR), is cycled between one or more refrigeration compressors 3 and cryogenic condensers 4 by streams 24 and 26, wherein the natural gas is cooled and condensed into a liquefied natural gas (LNG) stream 30 and inert gases such as nitrogen are separated from the natural gas and recovered via inert gas stream 31. Typically, a portion of the treated natural gas stream 18, and/or optionally a portion of untreated natural gas stream 10, is fed via stream 22 to the cryogenic liquefaction unit and used to fuel gas turbines, which in turn drive the refrigeration compressors. Flue gas stream 28 comprising primarily nitrogen, carbon dioxide and water is produced from the combustion of natural gas in the gas turbines.

Figure 1B:
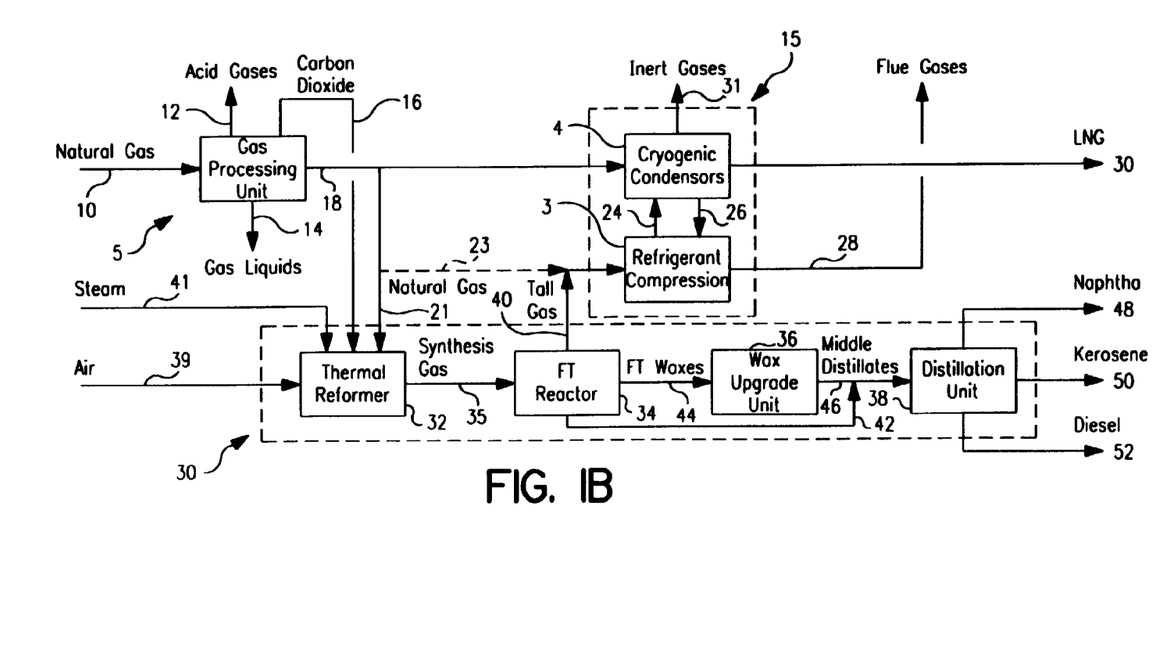
FIG. 1B is a process flow diagram of a Fischer-Tropsch process integrated with a process for liquefying natural gas.

A Fischer-Tropsch (FT) process 30 is shown in FIG. 1B and comprises a thermal reformer 32 and a FT reactor 34. Thermal reformer as used herein means any one of a number of known devices for reforming natural gas in the presence of oxygen into synthesis gas comprising carbon monoxide and hydrogen. Examples of thermal reformers include steam reformers, partial oxidation reformers, and autothermal reformers.

Figure 4:
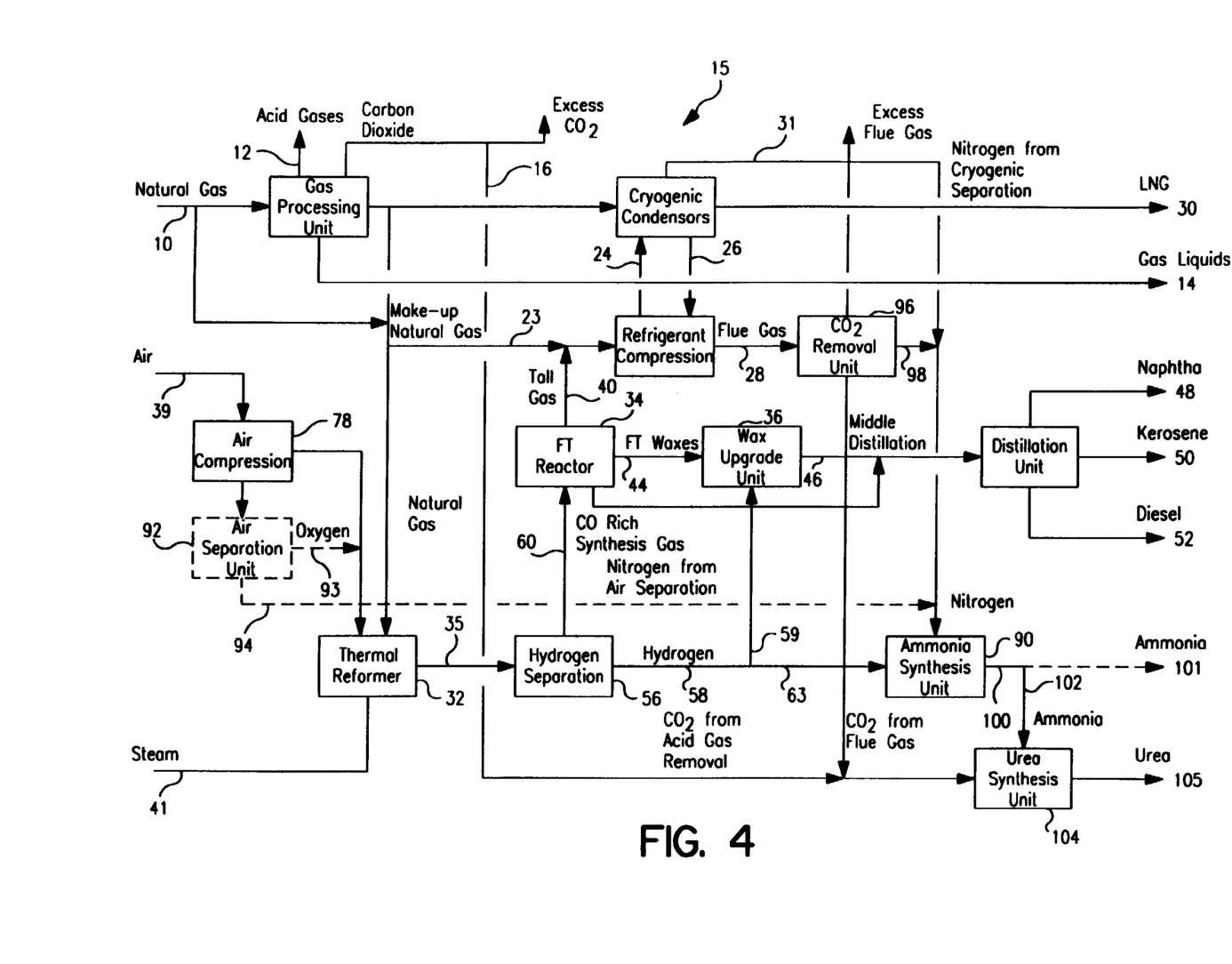
FIG. 4 is a process flow diagram of the integrated process of FIG. 1B further integrated with a fertilizer production process, wherein a single reformer is employed.

In a high-temperature steam reformer, methane and steam are reacted endothermically over a catalyst contained within a plurality of externally-heated tubes mounted in a large fired furnace. In a partial oxidation reformer, methane is exothermically reacted with purified oxygen, which requires an oxygen production unit such as an air separation unit. Autothermal reforming employs a combination of partial oxidation and steam reforming. The endothermic heat required for the steam reforming reaction is obtained from the exothermic partial oxidation reaction. Typically, air is used as the source of oxygen for the partial oxidation reaction in an autothermal reformer. The air is usually compressed and may be pretreated to remove a portion of the nitrogen, thereby enriching the air with a greater concentration of oxygen, as shown in FIG. 4. Synthesis gas produced by autothermal reforming usually contains substantial quantities of nitrogen from the inlet air.

Natural gas stream 21 containing methane is fed to thermal reformer 32, preferably an autothermal reformer, along with air stream 39 and steam stream 41 wherein the mixture is heated and reacted in the presence of a catalyst. The exothermic nature of the reaction increases the reaction temperature to between 1300 and 1850° F. The synthesis gas stream 35 produced from the autothermal reactor comprises synthesis gas (carbon monoxide and hydrogen) as well as combustion by-products (carbon dioxide and water) and inerts (nitrogen). Synthesis gas stream 35 is fed from the thermal reformer to a Fischer-Tropsch (FT) reactor 34 containing a Fischer-Tropsch catalyst. Examples of FT reactors suitable for use include slurry-bubble reactors and fixed bed reactors, such as tubular reactors.

In a slurry-bubble reactor, the liquid phase is molten hydrocarbon wax, and an FT catalyst is suspended in the liquid phase by the motion of bubbles of synthesis gas sparged into the bottom of the reactor. Heat is removed by cooling coils immersed in the slurry. In a fixed bed reactor, the FT catalyst is held in a fixed bed that is suspended within the FT reactor vessel, and the reactants flow through the reactor vessel and contact the FT catalyst held in the fixed bed. Removal of reaction heat is accomplished by a cooling medium flowing around the tubes or vessels containing the fixed bed.

In the FT reactor, carbon monoxide and hydrogen combine in a polymerization-like fashion to form hydrocarbon compounds having varying numbers of carbon atoms. The hydrocarbon compounds are typically separated into three streams (often by boiling point), with each stream having the majority of the hydrocarbons falling within a given range of carbon atoms. The FT tail gas stream 40 typically comprises gaseous light compounds having about one to six carbon atoms, and in the case of an air blown thermal reforming process, is comprised primarily of inerts. The FT tail gas generally has a low heat value, typically having a caloric value of less than about 200 BTU/SCF. The FT liquids stream 42 typically comprises liquid intermediate compounds, such as synthetic crude or paraffinic liquids, having about five to seventeen carbon atoms. The FT wax stream 44 comprises solid or semi-solid heavy compounds, such as waxy hydrocarbons, having greater than about seventeen carbon atoms. It should be understood that the split of compounds between the streams 40, 42, and 44 is subject to some overlap and can be optimized based upon the operating conditions of the FT reactor.

The FT process 30 may further comprise a wax upgrading unit 36 and a distillation unit 38. In the wax upgrading unit, FT wax stream 44 from FT reactor 34 is upgraded by a hydrotreater, a hydrocracker, or a combination of both a hydrotreater and a hydrocracker. Middle distillates stream 46 is produced by the hydrogenation and shortening of the long-chain hydrocarbon FT waxes in the hydrotreater and/or the thermal degradation of FT waxes in the presence of hydrogen in the hydrocracker.

Figure 2:
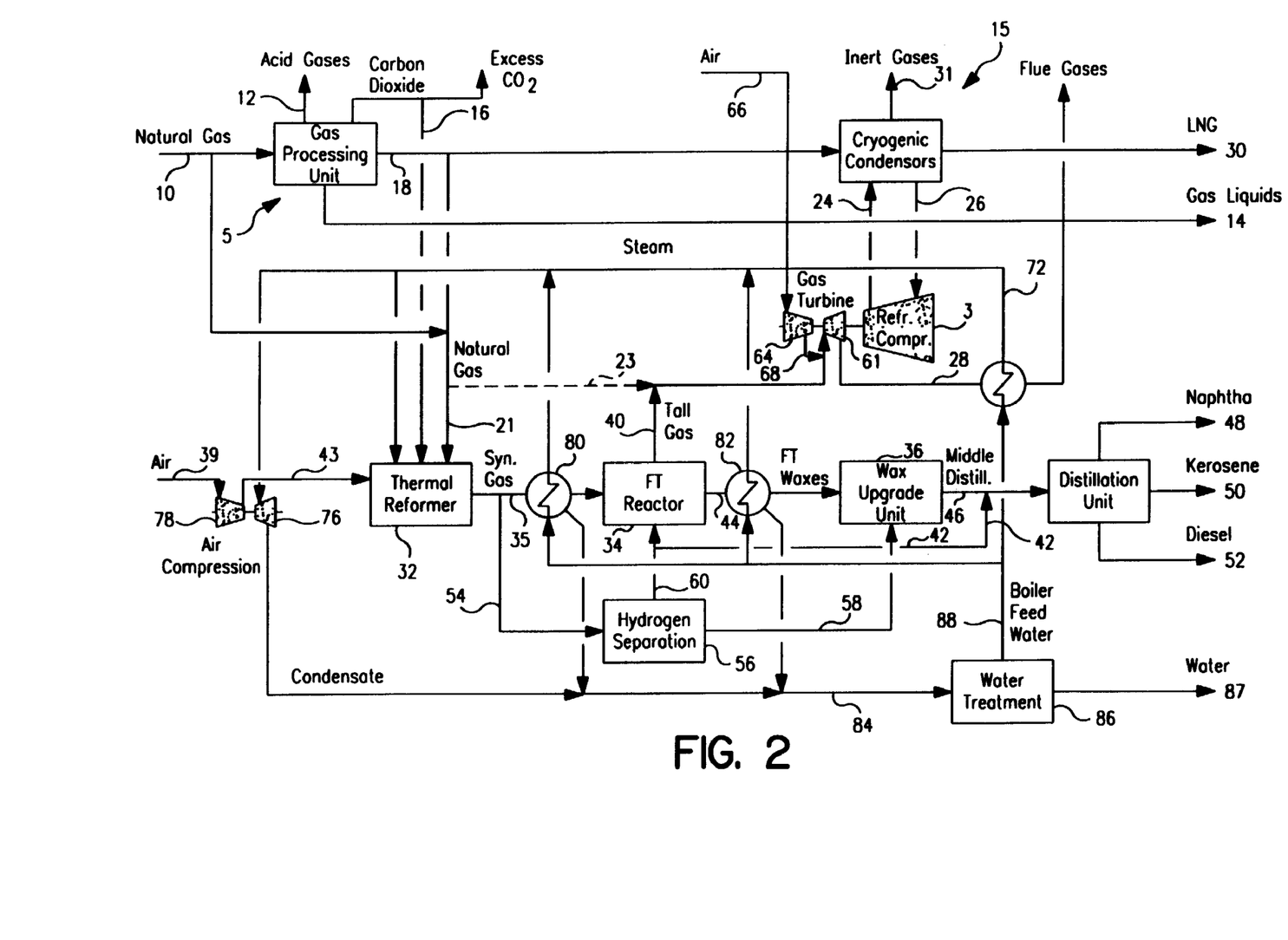
FIG. 2 is a preferred embodiment of the integrated process of FIG. 1B employing a gas turbine.

Hydrogen for hydrotreating and/or hydrocracking is separated from the synthesis gas as shown in FIG. 2, and a like hydrogen separation process may be employed in the process according to FIG. 1B. A slip stream 54 of synthesis gas is fed to hydrogen separator 56, wherein hydrogen is separated from the synthesis gas and fed via stream 58 to wax upgrading unit 36. The amount of synthesis gas fed to the hydrogen separator can be optimized based upon the demand for hydrogen and the operating efficiency of the hydrogen separation technology employed. Synthesis gas exiting the hydrogen separator and having a reduced hydrogen concentration is fed to the FT reactor 34 via stream 60. Any of several known methods can be used to separate hydrogen from the synthesis gas, including membrane separation (both polymeric membranes such as polysolfone fiber, polyamides or halogenated polycarbonates, and metal membranes such as a palladium thimble) or pressure swing adsorption.

The middle distillates stream 46 and the FT liquids stream 42 may be further separated in distillation unit 38 to produce product streams such as naphtha stream 48, kerosene stream 50, and diesel stream 52. The naphtha, kerosene, and diesel streams are essentially free of sulfur and thus are valuable as blending stock for producing enviromnentally-friendly low sulfur diesel fuels.

An integrated FT/LNG process in accordance with the invention is shown in FIG. 1B. FT tail gas stream 40 is used to fuel turbines, which in turn drive the refrigeration compressors 3 in the LNG process. The energy is extracted from the FT tail gas by means of a gas turbine as shown in FIG. 2 or a steam turbine as shown in FIG. 3.

In a preferred embodiment shown in FIG. 2, tail gas stream 40 fuels gas turbine 61 to drive refrigeration compressor 3 in cryogenic liquefaction unit 15. Gas turbine 61 operates by either expanding the FT tail gas from a higher to a lower pressure, combusting the FT tail gas, or both. Optionally, natural gas stream 23 can be used to supplement the FT tail gas feed to the gas turbine, and the supplemental natural gas may be either raw, treated, or a combination thereof. An appropriate number of gas turbines and refrigeration compressors can be employed to meet the capacity requirements for a given unit. Gas turbine 60 also drives air compressor 64 used to increase the pressure of combustion air fed via stream 66. The high pressure combustion air exiting air compressor 64 is mixed with the tail gas, and optionally supplemental natural gas, such that a combustible mixture of gas and oxygen enters the combustion chamber of turbine 61, wherein the mixture is combusted to drive air compressor 64 and refrigeration compressor 3.

Figure 3:
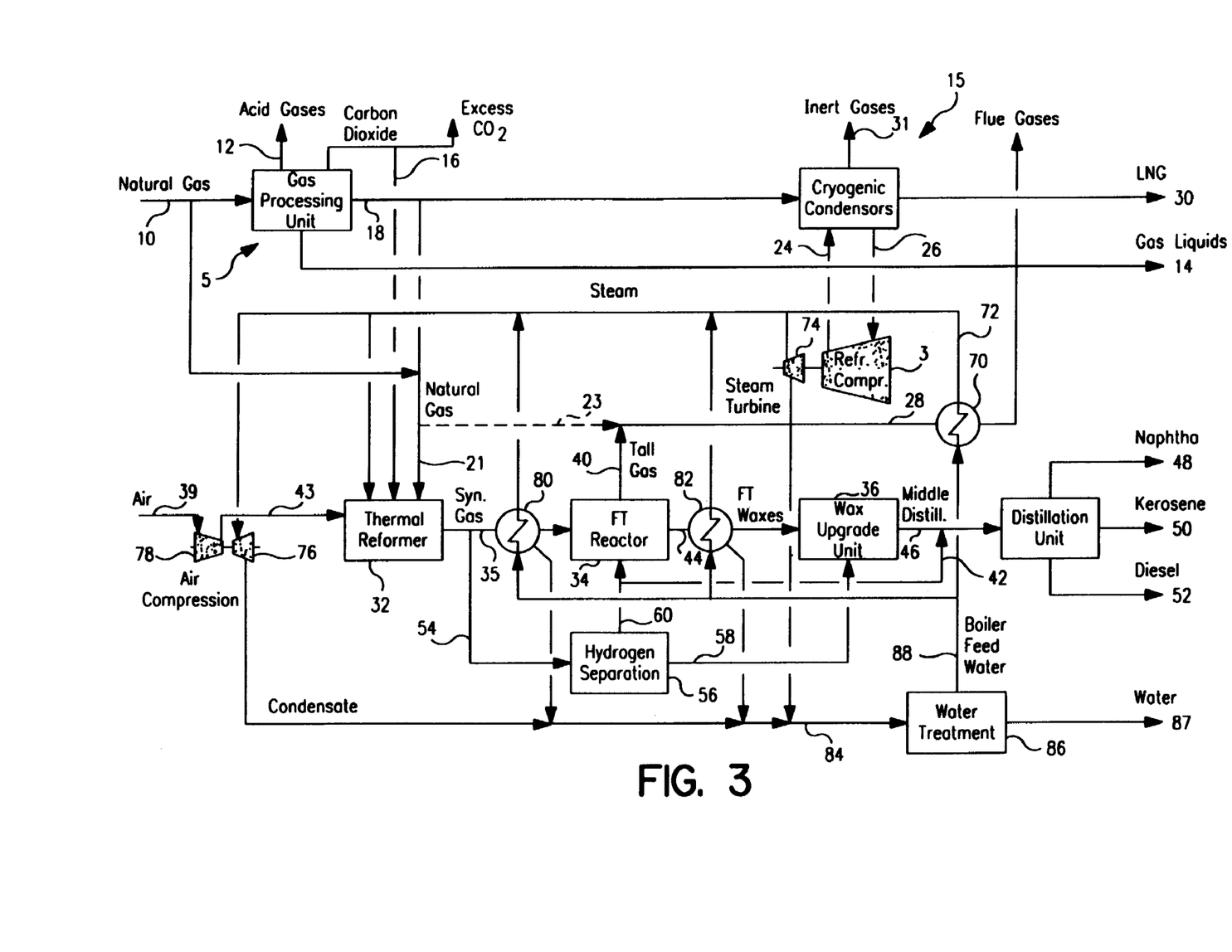
FIG. 3 is a preferred embodiment of the integrated process of FIG. 1B employing a steam turbine.

In a preferred embodiment shown in FIG. 3, FT tail gas stream 40 is combusted in steam boiler 70 to generate steam stream 72, which supplies steam to steam turbine 74 driving refrigeration compressor 3 in cryogenic liquefaction unit 15. Optionally, natural gas stream 23 can be used to supplement the FT tail gas feed to steam boiler 70, and the supplemental natural gas may be either raw, treated, or a combination thereof.

As shown in FIGS. 2 and 3, steam from stream 72 can be supplied to steam turbine 76, which in turn drives air compressor 78, wherein air from stream 39 is compressed prior to being fed via stream 43 to thermal reformer 32. Syngas waste heat boiler 80 and is FT reactor waste heat boiler 82 can be used to generate stream via recovery of waste heat from synthesis gas stream 35 and FT wax stream 44, respectively. Although not shown in the figures, FT liquids stream 42 and middle distillates stream 46 may also be used as a source of heat in steam generation. As shown in FIG. 2, heat exchanger 71 can be used to generate steam from flue gas stream 28 exiting gas turbine 61.

In the integrated FT/LNG processes of FIGS. 1B, 2, and 3, carbon dioxide stream 16 from gas processing unit 5 is fed to thermal reformer 32. In the presence of steam, carbon dioxide in the thermal reformer will be converted to carbon monoxide and hydrogen. The amount of carbon dioxide to be reformed may vary depending upon energy costs and the composition of the raw natural gas, but typically between about 15 to 25% by volume of the carbon dioxide produced in gas processing unit 5 may be reformed economically in thermal reformer 32.

Where beneficial, such as processing gas in arid or remote locations, water can be recovered from the integrated process of this invention, as shown in FIGS. 2 and 3. Water generated in thermal reformer 32 is condensed and removed from synthesis gas stream 35 by cooling the stream in syngas waste heat boiler 80 and subsequent further cooling with air or cooling water. Water generated in FT reactor 34 is condensed and removed from FT wax stream 44 by cooling the stream in FT reactor waste heat boiler 82 and subsequent further cooling with air or cooling water. Water from boilers 80 and 82 is fed by stream 84 to water treatment plant 86, wherein treated water is recovered via stream 87 and boiler feed water is recycled via stream 88 to the steam generation heat exchangers and/or boilers. Not shown in the diagrams, steam may be produced in separate circuits at different levels of pressure and temperature for purposes of optimizing heat recovery efficiencies. Also not shown, organic contaminants from process condensate preferably will be concentrated in a separate stream and used to produce steam for reforming purposes.

Figure 5:
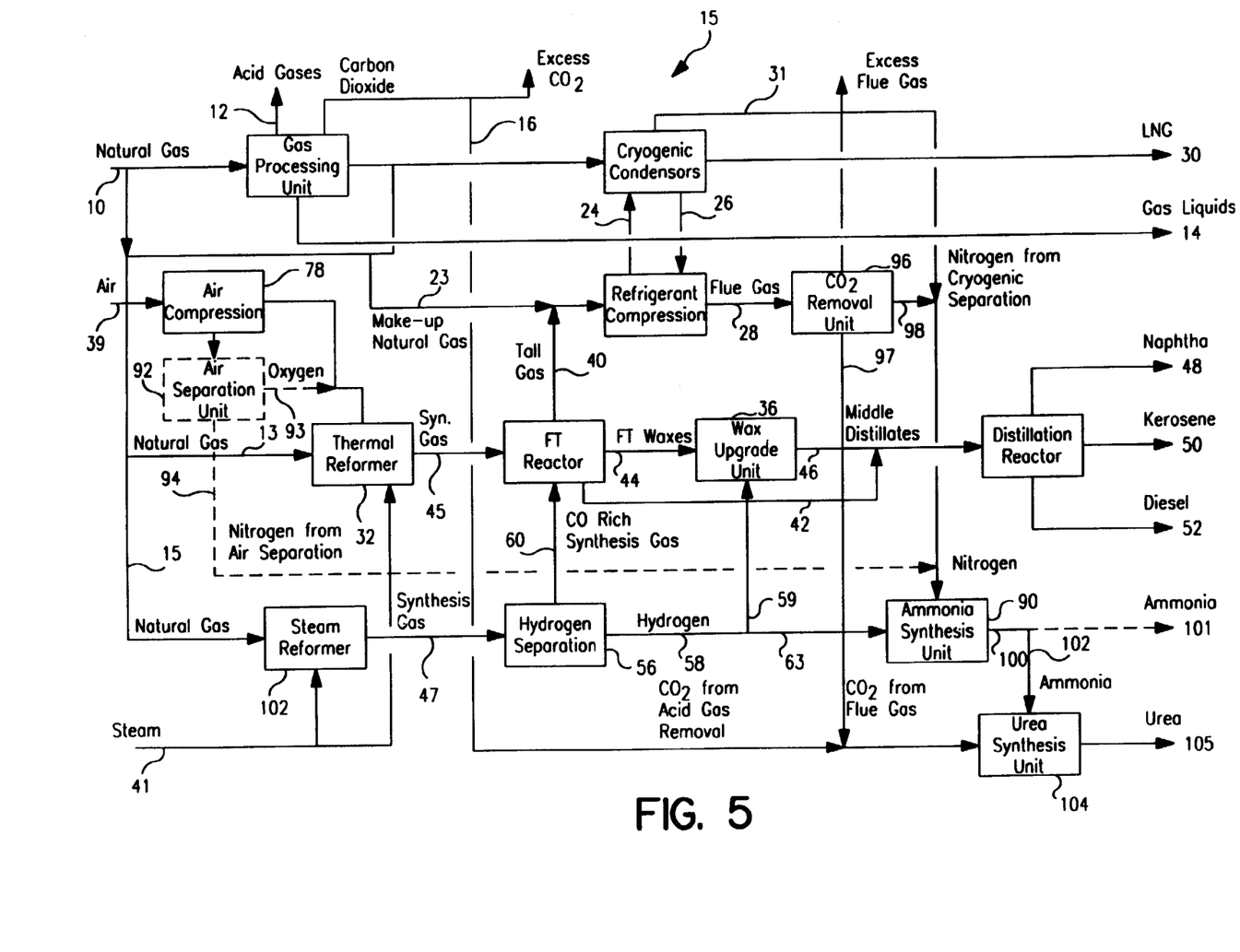
FIG. 5 is a process flow diagram of the integrated process of FIG. 1B further integrated with a fertilizer production process, wherein dual reformers are employed.

In preferred embodiments according to this invention shown in FIGS. 4 and 5, the integrated FT/LNG process of FIG. 1B is further integrated to include a fertilizer production process comprising an ammonia synthesis process and a urea synthesis process. Specifically, hydrogen and nitrogen from the integrated FT/LNG process are combined to produce ammonia, which is subsequently reacted with carbon dioxide to produce urea, commonly used as a fertilizer.

As shown in FIGS. 4 and 5, hydrogen stream 58 exiting hydrogen separator 56 is split whereby a portion is fed via stream 59 to wax upgrading unit 36 and a portion is fed via stream 63 to ammonia synthesis unit 90. Nitrogen may be fed to ammonia synthesis unit 90 from either cryogenic liquefication unit 15, air separation unit 92, carbon dioxide removal unit 96, or any combination thereof. Inert gas stream 31, produced during the cryogenic liquefaction of natural gas and comprising primarily nitrogen, is fed to ammonia synthesis unit 90. A portion of the compressed air exiting compressor 78 may be fed to air separation unit 92, thereby producing stream 93 comprised primarily of oxygen and stream 94 comprised primarily of nitrogen. Oxygen stream 93 is used to enrich the compressed air being fed to thermal reformer 32, and nitrogen stream 94 is fed to ammonia synthesis unit 90. Flue gas, comprising primarily carbon dioxide, nitrogen, and water produced either by combustion of tail gas in gas turbine 61 of FIG. 2 or combustion of tail gas in steam boiler 70 of FIG. 3, is fed via stream 28 to carbon dioxide removal unit 96, thereby producing stream 98 comprised primarily of nitrogen and stream 97 comprised primarily of carbon dioxide. Nitrogen stream 98 is fed to ammonia synthesis unit 90.

The integration of ammonia synthesis unit 90 results in an increased usage of hydrogen, which in turn requires an increased amount of synthesis gas from which the hydrogen is separated. To meet the increased demand for synthesis gas, a single thermal reformer can be scaled up to produce enough hydrogen for use in wax upgrading unit 36, ammonia synthesis unit 90, and FT reactor 34. As shown in FIG. 4, synthesis gas from a single thermal reformer 32, preferably an autothermal reformer, is fed via stream 35 to hydrogen separator 56, wherein a portion of the hydrogen is removed from the synthesis gas and conveyed as a concentrated hydrogen stream 58 and the remaining hydrogen contained in carbon monoxide rich synthesis gas stream 60 is fed to FT reactor 34. A portion of synthesis gas stream 35 may be bypassed directly to FT reactor 34, as shown in FIG. 2. Carbon monoxide rich synthesis gas stream 60 must contain sufficient hydrogen to fuel the FT reaction, and thus the ratio of hydrogen to carbon monoxide in stream 60 should be no less than about 2:1.

Alternatively, dual reformers can be employed to meet the increased demand for synthesis gas. As shown in FIG. 5, primary thermal reformer 32, preferably an autothermal reformer, can be used to produce synthesis gas stream 45 which is fed to FT reactor 34, and secondary thermal reformer 106, preferably a steam reformer, can be used to produce synthesis gas stream 47 which is fed to hydrogen separator 56.

The hydrogen and nitrogen are reacted in ammonia synthesis unit 90 according to known methods to produce ammonia stream 100, from which ammonia product can be recovered via stream 101 and/or ammonia can be fed via stream 102 to urea synthesis unit 104. Carbon dioxide is fed to the urea synthesis unit 104 via stream 16 from gas processing unit 5 and/or stream 97 from carbon dioxide removal unit 96, wherein it is reacted with ammonia to produce urea product stream 105. While urea is commonly used as a fertilizer, urea produced according to this invention is not limited to such use and may be used for any known purpose.

The tail gas integration shown in FIGS. 4 and 5 can be in accordance with either the steam turbine system of FIG. 3 or the gas turbine system of FIG. 2. The most preferred embodiment is the single reformer embodiment of FIG. 4 combined with either the gas turbine system of FIG. 2 or the steam turbine system of FIG. 3.

Figure 6:
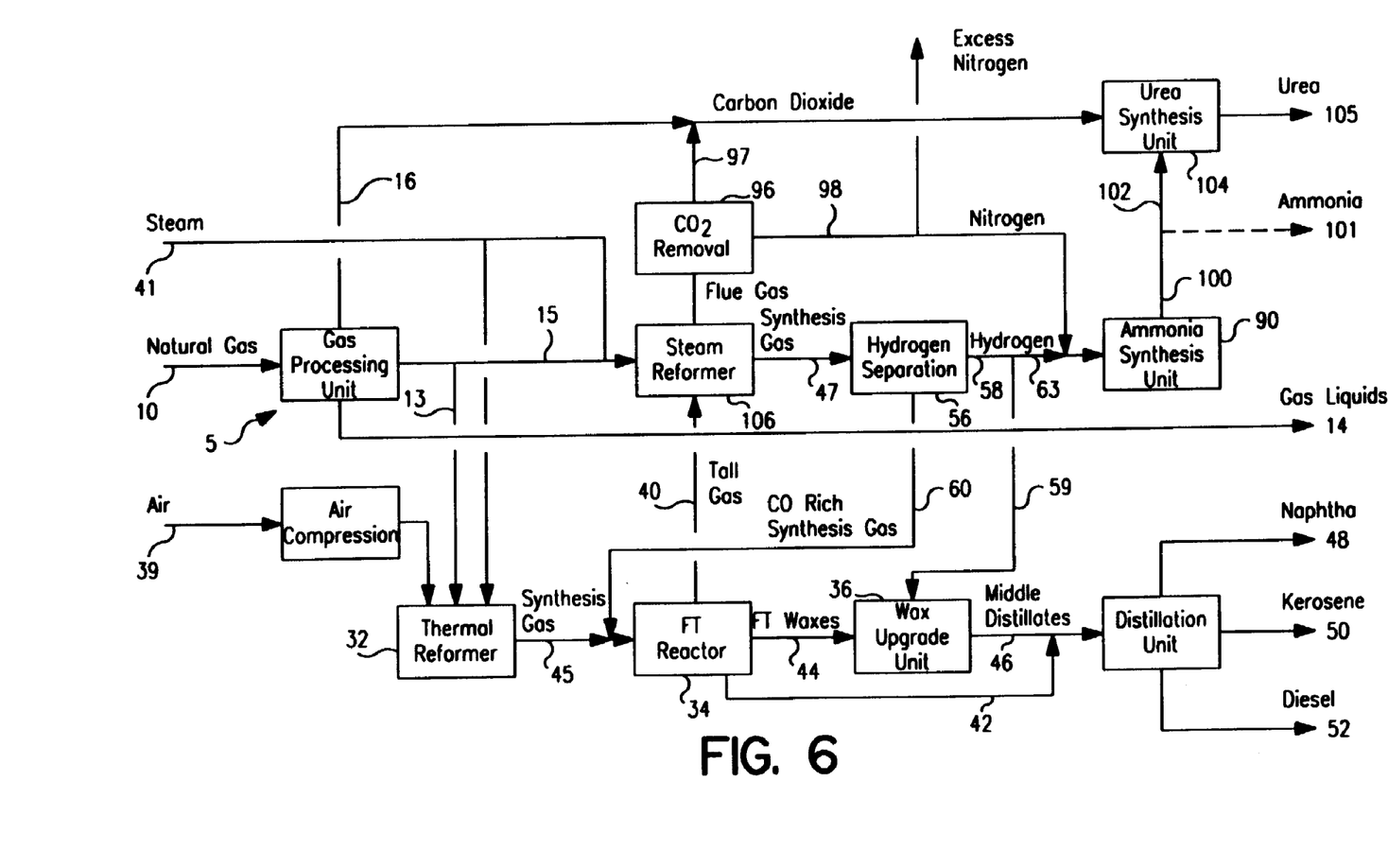
FIG. 6 is a process flow diagram of a Fischer-Tropsch process integrated with a fertilizer production process.

An alternative embodiment shown in FIG. 6 is the integration of an FT process with a fertilizer process, in the absence of an LNG process, wherein tail gas stream 40 is used to fuel burners in steam reformer 106 rather than being used to fuel the turbines driving the refrigeration compressors in the LNG unit. Dual reformers are used in the integrated FT/Fertilizer process, similar to the dual reformers employed in the integrated FT/LNG/Fertilizer process of FIG. 5. Natural gas stream 10 is processed in gas processing unit 5, and processed natural gas is fed via stream 15 to steam reformer 106 and via stream 13 to thermal reformer 32, preferably an autothermal reformer. Synthesis gas stream 47 from steam reformer 106 is fed to hydrogen separator 56. Hydrogen stream 58 exiting hydrogen separator 56 is split whereby a portion is fed via stream 59 to wax upgrading unit 36 and a portion is fed via stream 63 to ammonia synthesis unit 90.

Carbon monoxide rich synthesis gas stream 60 from hydrogen separator 56 and synthesis gas stream 45 from thermal reformer 32 are fed to FT reactor 34. Tail gas stream 40 from FT reactor 34 is used to fuel burners in steam reformer 106, with optional make-up natural gas stream (not shown) providing supplemental fuel to the steam reformer burners as needed. As previously described herein, products from the FT reactor are treated and recovered, and hydrogen from stream 63 and nitrogen from stream 98 are reacted in ammonia synthesis unit 90 to produce ammonia. The ammonia may be recovered as a product or further reacted with carbon dioxide from stream 16 and/or stream 97 in urea synthesis unit 104 to produce urea.

Figure 7:
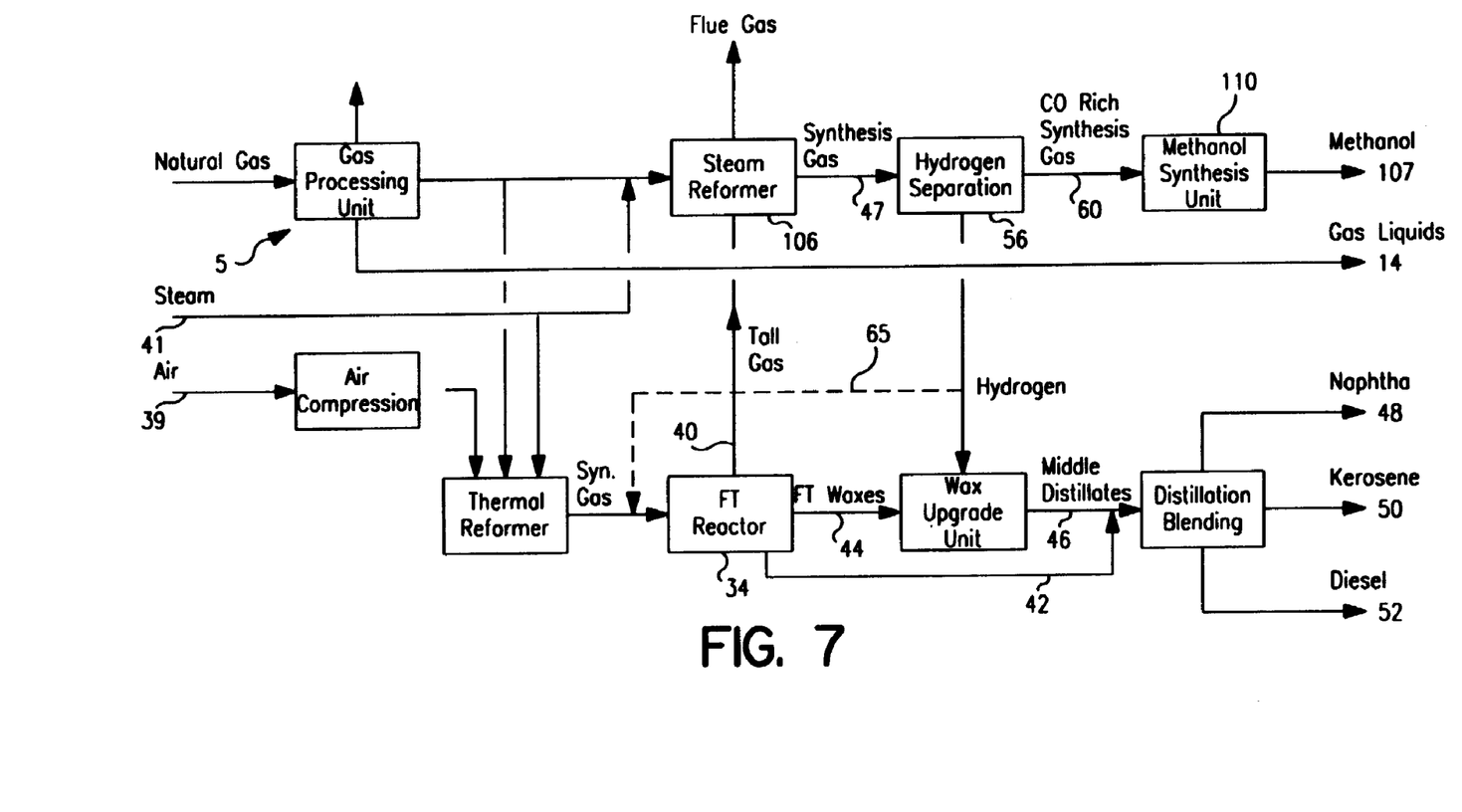
FIG. 7 is a process flow diagram of a Fischer-Tropsch process integrated with a methanol synthesis process.

An alternative embodiment shown in FIG. 7 is the integration of an FT process with a methanol process. Dual reformers are used in the integrated FT/methanol process, similar to the dual reformers employed in the integrated FT/Fertilizer process of FIG. 6. Like the integrated FT/Fertilizer process, the natural gas is processed in a gas processing unit 5 prior to being fed to the reformers, and tail gas stream 40 from FT reactor 56 is used to fuel burners in steam reformer 106. Also, hydrogen separator 56 is used to remove hydrogen from synthesis gas supplied by stream 47 from steam reformer 106. However, instead of using carbon monoxide rich synthesis gas in FT reactor 34 as shown in FIG. 6, the FT/Methanol integrated process of FIG. 7 feeds carbon monoxide rich synthesis gas stream 60 to methanol synthesis unit 110, wherein methanol recovered via stream 107 is produced according to known processes. Also, the integrated FT/Methanol process feeds excess hydrogen via stream 65 from hydrogen separator 56 to FT reactor 34.

What is claimed is:

1. An integrated process for converting hydrocarbon gas to liquids, comprising:
   (a) liquefying natural gas in a cryogenic liquefaction unit;
   (b) reforming natural gas into synthesis gas;
   (c) reacting the synthesis gas with a Fischer-Tropsch catalyst to produce liquid hydrocarbons and tail gas;
   (d) driving a refrigeration compressor in the cryogenic liquefaction unit with the tail gas; and
   (e) recovering liquefied natural gas and liquid hydrocarbons.

2. The integrated process of claim 1 further comprising processing the natural gas prior to steps (a) and (b).

3. The integrated process of claim 1 further comprising feeding to the reformer carbon dioxide removed during the natural gas processing.

4. The integrated process of claim 1 further comprising separating hydrogen from the synthesis gas, supplying exhaust synthesis gas from the hydrogen separator to the Fischer-Tropsch reactor, and supplying the hydrogen to a unit selected from the group consisting of a hydrocracker, a hydrotreater, and an ammonia synthesis unit.

5. The integrated process of claim 4 wherein the hydrogen is separated from the synthesis gas by pressure swing absorption or a membrane.

6. The integrated process of claim 1 further comprising secondarily reforming natural gas into additional synthesis gas, separating hydrogen from the additional synthesis gas, supplying exhaust synthesis gas from the hydrogen separator to the Fischer-Tropsch reactor, and supplying the hydrogen to a unit selected from the group consisting of a hydrocracker, a hydrotreater, and an ammonia synthesis unit.

7. The integrated process of claim 6 wherein the hydrogen is separated from the synthesis gas by pressure swing absorption or a membrane.

8. The integrated process of claim 1 further comprising secondarily reforming natural gas into additional synthesis gas, separating hydrogen from the additional synthesis gas produced by the secondary reformation of natural gas and from the synthesis gas produced by the primary reformation of natural gas, supplying exhaust synthesis gas from the hydrogen separator to the Fischer-Tropsch reactor, and supplying the hydrogen to a unit selected from the group consisting of a hydrocracker, a hydrotreater, and an ammonia synthesis unit.

9. The integrated process of claim 4 further comprising removing carbon dioxide from flue gas from a gas turbine driving the refrigeration compressor in the cryogenic liquefaction unit, subsequently supplying the flue gas to an ammonia synthesis unit, supplying the carbon dioxide to a urea synthesis unit, and supplying ammonia from the ammonia synthesis unit to the urea synthesis unit.

10. The integrated process of claim 6 further comprising removing carbon dioxide from flue gas from a gas turbine driving the refrigeration compressor in the cryogenic liquefaction unit, subsequently supplying the flue gas to an ammonia synthesis unit, supplying the carbon dioxide to a urea synthesis unit, and supplying ammonia from the ammonia synthesis unit to the urea synthesis unit.

11. The integrated process of claim 4 further comprising separating oxygen and nitrogen from air, supplying the oxygen to the reformer, and supplying the nitrogen to an ammonia synthesis unit.

12. The integrated process of claim 6 further comprising separating oxygen and nitrogen from air, supplying the oxygen to the reformer, and supplying the nitrogen to an ammonia synthesis unit.

13. The integrated process of claim 9 further comprising separating oxygen and nitrogen from air, supplying the oxygen to the reformer, and supplying the nitrogen to the ammonia synthesis unit.

14. The integrated process of claim 10 further comprising separating oxygen and nitrogen from air, supplying the oxygen to the reformer, and supplying the nitrogen to the ammonia synthesis unit.

15. The integrated process of claim 9 further comprising supplying nitrogen removed from the natural gas in the cryogenic liquefaction unit to the ammonia synthesis unit.

16. The integrated process of claim 10 further comprising supplying nitrogen removed from the natural gas in the cryogenic liquefaction unit to the ammonia synthesis unit.

17. The integrated process of claim 11 further comprising supplying nitrogen removed from the natural gas in the cryogenic liquefaction unit to the ammonia synthesis unit.

18. The integrated process of claim 12 further comprising supplying nitrogen removed from the natural gas in the cryogenic liquefaction unit to the ammonia synthesis unit.

19. The integrated process of claim 13 further comprising supplying nitrogen removed from the natural gas in the cryogenic liquefaction unit to the ammonia synthesis unit.

20. The integrated process of claim 14 further comprising supplying nitrogen removed from the natural gas in the cryogenic liquefaction unit to the ammonia synthesis unit.

21. The integrated process of claim 1 further comprising removing carbon dioxide from the natural gas prior to its being liquefied and supplying the carbon dioxide to the reformer.

22. The integrated process of claim 9 further comprising removing carbon dioxide from the natural gas prior to its being liquefied and supplying the carbon dioxide to the urea synthesis unit.

23. The integrated process of claim 10 further comprising removing carbon dioxide from the natural gas prior to its being liquefied and supplying the carbon dioxide to the urea synthesis unit.

24. The integrated process of claim 11 further comprising removing carbon dioxide from the natural gas prior to its being liquefied, supplying the carbon dioxide to a urea synthesis unit, and supplying ammonia from the ammonia synthesis unit to the urea synthesis unit.

25. The integrated process of claim 12 further comprising removing carbon dioxide from the natural gas prior to its being liquefied, supplying the carbon dioxide to a urea synthesis unit, and supplying ammonia from the ammonia synthesis unit to the urea synthesis unit.

26. The integrated process of claim 13 further comprising removing carbon dioxide from the natural gas prior to its being liquefied and supplying the carbon dioxide to the urea synthesis unit.

27. The integrated process of claim 14 further comprising removing carbon dioxide from the natural gas prior to its being liquefied and supplying the carbon dioxide to the urea synthesis unit.

28. The integrated process of claim 15 further comprising removing carbon dioxide from the natural gas prior to its being liquefied and supplying the carbon dioxide to the urea synthesis unit.

29. The integrated process of claim 16 further comprising removing carbon dioxide from the natural gas prior to its being liquefied and supplying the carbon dioxide to the urea synthesis unit.

30. The integrated process of claim 17 further comprising removing carbon dioxide from the natural gas prior to its being liquefied, supplying the carbon dioxide to a urea synthesis unit, and supplying ammonia from the ammonia synthesis unit to the urea synthesis unit.

31. The integrated process of claim 18 further comprising removing carbon dioxide from the natural gas prior to its being liquefied, supplying the carbon dioxide to a urea synthesis unit, and supplying ammonia from the ammonia synthesis unit to the urea synthesis unit.

32. The integrated process of claim 19 further comprising removing carbon dioxide from the natural gas prior to its being liquefied and supplying the carbon dioxide to the urea synthesis unit.

33. The integrated process of claim 20 further comprising removing carbon dioxide from the natural gas prior to its being liquefied and supplying the carbon dioxide to the urea synthesis unit.

34. An integrated process for converting hydrocarbon gas to liquids, comprising:
    (a) removing carbon dioxide from natural gas;
    (b) liquefying natural gas from step (a) in a cryogenic liquefaction unit, wherein nitrogen is produced;
    (c) supplying nitrogen from step (b) to an ammonia synthesis unit;
    (d) supplying carbon dioxide from step (a) to a urea synthesis unit;
    (e) supplying ammonia from the ammonia synthesis unit to the urea synthesis unit;
    (f) reforming natural gas into synthesis gas;
    (g) separating hydrogen from the synthesis gas;
    (h) reacting the synthesis gas with a Fisher-Tropsch catalyst to produce liquid hydrocarbons and tail gas;
    (i) driving a refrigeration compressor in the cryogenic liquefaction unit with the tail gas;
    (j) upgrading the liquid hydrocarbons from the Fischer-Tropsch reaction by contacting the liquid hydrocarbons with hydrogen from step (g);
    (k) supplying hydrogen from step (g) to the ammonia synthesis unit;
    (l) removing carbon dioxide from flue gas from a gas turbine driving the refrigeration compressor in the cryogenic liquefaction unit;
    (m) supplying carbon dioxide from step (l) to the urea synthesis unit;
    (n) supplying exhaust flue gas from step (l) to the ammonia synthesis; and
    (o) recovering urea from the urea synthesis unit, liquefied natural gas from the cryogenic separation unit, and liquid hydrocarbons.

35. The integrated process of claim 34 further comprising separating oxygen and nitrogen from air, supplying the oxygen to the reformer, and supplying the nitrogen to the ammonia synthesis unit.

36. The integrated process of claim 34 further comprising recovering ammonia from the ammonia synthesis unit.

37. The integrated process of claim 36 further comprising distilling the upgraded liquid hydrocarbons and recovering naphtha, kerosene and diesel.

38. An integrated process for liquefying hydrocarbon gas comprising driving a refrigeration compressor in a cryogenic liquefaction unit with tail gas from a Fischer-Tropsch reaction.

39. The integrated process of claim 38 further comprising removing hydrogen from synthesis gas prior its being supplied to the Fischer-Tropsch reaction and using the hydrogen to synthesize ammonia and treat liquid hydrocarbons from the Fischer-Tropsch reaction.

40. The integrated process of claim 39 further comprising synthesizing the ammonia by reacting the hydrogen with nitrogen removed from the natural gas in the cryogenic liquefaction unit and nitrogen contained in flue gas from a gas turbine driving the refrigeration compressor.

41. The integrated process of claim 40 further comprising synthesizing urea by reacting the ammonia with carbon dioxide removed from the natural gas prior to its being liquefied and with carbon dioxide removed from the flue gas from a gas turbine driving the refrigeration compressor.

42. The integrated process of claim 41 further comprising separating oxygen and nitrogen from air, using the oxygen to produce synthesis gas, and using the nitrogen to synthesize ammonia.

43. An integrated process for converting hydrocarbon gas to liquids, comprising:
    (a) removing carbon dioxide from natural gas;
    (b) supplying carbon dioxide from step (a) to a urea synthesis unit;
    (c) primarily reforming natural gas into synthesis gas;
    (d) secondarily reforming natural gas into additional synthesis gas;
    (e) separating hydrogen from the additional synthesis gas produced in step (d), thereby producing dehydrogenated synthesis gas;
    (f) reacting the synthesis gas from step (c) and the dehydrogenated synthesis gas from step (e) with a Fisher-Tropsch catalyst to produce liquid hydrocarbons and tail gas;

(g) fueling the secondary reformer used in step (d) with the tail gas;

(h) upgrading the liquid hydrocarbons from the Fischer-Tropsch reaction by contacting the liquid hydrocarbons with hydrogen from step (e);

(i) supplying hydrogen from step (e) to an ammonia synthesis unit;

(j) removing carbon dioxide from flue gas from the secondary reformer, thereby producing nitrogen-enriched flue gas;

(k) supplying carbon dioxide from step (j) to the urea synthesis unit;

(l) supplying the nitrogen-enriched flue gas from step (j) to the ammonia synthesis;

(m) supplying ammonia from the ammonia synthesis unit to the urea synthesis unit; and (n) recovering urea and liquid hydrocarbons.

44. The integrated process of claim 43 wherein the primary reformer is an auto-thermal reformer and the secondary reformer is a steam reformer.

45. The integrated process of claim 44 wherein natural gas having carbon dioxide removed in step (a) is reformed in steps (c) and (d).

46. An integrated process for converting hydrocarbon gas to liquids, comprising:

(a) primarily reforming natural gas into synthesis gas;

(b) secondarily reforming natural gas into additional synthesis gas;

(c) separating hydrogen from the additional synthesis gas produced in step (b), thereby producing carbon monoxide rich synthesis gas;

(d) producing methanol from the carbon monoxide rich synthesis gas;

(e) reacting the synthesis gas from step (a) with a Fischer-Tropsch catalyst to produce liquid hydrocarbons and tail gas;

(f) fueling the secondary reformer used in step (b) with the tail gas;

(g) upgrading the liquid hydrocarbons from the Fischer-Tropsch reaction by contacting the liquid hydrocarbons with hydrogen from step (c); and (h) recovering methanol and liquid hydrocarbons.

47. The integrated process of claim 46 wherein the primary reformer is an auto-thermal reformer and the secondary reformer is a steam reformer.

48. The integrated process of claim 47 further comprising supplying hydrogen from step (c) to the Fischer-Tropsch reaction.

* * * * *